United States Patent [19]

Merger et al.

[11] Patent Number: 6,140,545
[45] Date of Patent: Oct. 31, 2000

[54] PREPARATION OF ALCOHOLS

[75] Inventors: Martin Merger, Frankenthal; Shelue Liang, Ludwigshafen; Rolf Fischer, Heidelberg; Joachim Wulff-Döring, Frankenthal, all of Germany

[73] Assignee: BASF Aktiengesellschaft, Ludwigshfen, Germany

[21] Appl. No.: 09/251,462

[22] Filed: Feb. 17, 1999

[30] Foreign Application Priority Data

Feb. 20, 1998 [DE] Germany ............... 198 07 268

[51] Int. Cl.$^7$ .................................................. C07C 37/08
[52] U.S. Cl. ................. 568/799; 568/831; 568/855
[58] Field of Search ............................ 568/885, 831, 568/799

[56] References Cited

U.S. PATENT DOCUMENTS

| | | | |
|---|---|---|---|
| 3,361,832 | 1/1968 | Pine | 568/885 |
| 4,918,248 | 4/1990 | Hattori | 568/885 |
| 4,929,777 | 5/1990 | Irick | 568/885 |
| 5,008,235 | 4/1991 | Wegman et al. | 502/342 |
| 5,142,067 | 8/1992 | Wegman | 568/885 |
| 5,395,990 | 3/1995 | Scarlett | 568/864 |
| 5,403,962 | 4/1995 | Schneider | 568/885 |
| 5,475,159 | 12/1995 | Singleton | 568/885 |

FOREIGN PATENT DOCUMENTS

| | | |
|---|---|---|
| 285786 | 5/1993 | European Pat. Off. . |
| 585053 | 3/1994 | European Pat. Off. . |
| 4021230 | 1/1991 | Germany . |
| 62108832 | 11/1985 | Japan . |
| 06063401 | 8/1992 | Japan . |
| 06065125 | 8/1992 | Japan . |
| 1454440 | 11/1976 | United Kingdom . |
| 1551741 | 8/1979 | United Kingdom . |
| 97/31882 | 9/1997 | WIPO . |

*Primary Examiner*—Michael L. Shippen
*Attorney, Agent, or Firm*—Keil & Weinkauf

[57] ABSTRACT

In a process for preparing alcohols by gas phase hydrogenation of carboxylic acids or esters thereof at elevated temperature and elevated pressure in the presence of catalysts consisting of or comprising, as hydrogenating components, oxides of main group VI and/or subgroup IV, the hydrogenation is carried out a) at from 250° C. to 400° C. and from 5 bar to 100 bar in the presence of b) primary or secondary alcohols, the molar hydrogen/alcohol ratio being at most 800.

10 Claims, 1 Drawing Sheet

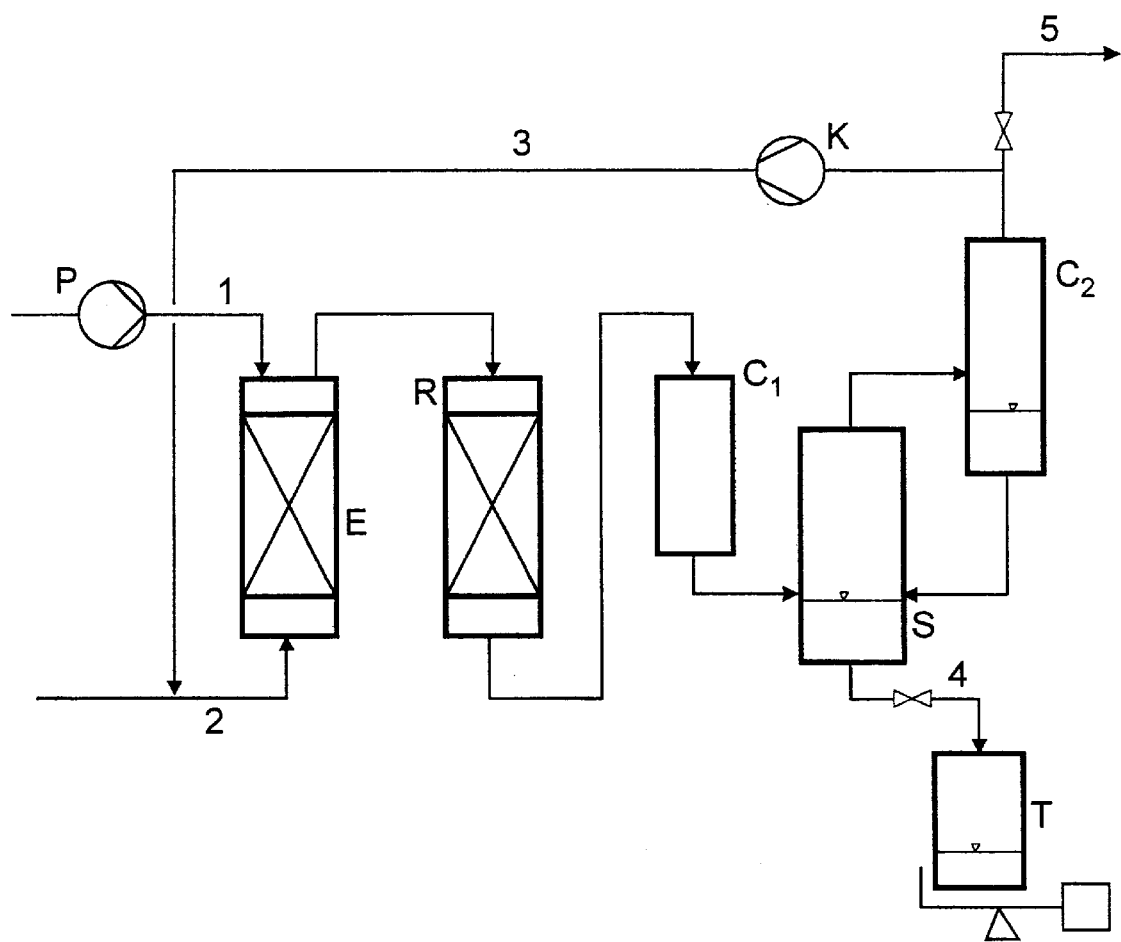

PREPARATION OF ALCOHOLS

The present invention relates to a process for preparing alcohols by gas phase hydrogenation of carboxylic acids or esters thereof at temperatures in the range from 250 to 400° C. and pressures in the range from 5 to 100 bar in the presence of a catalyst predominantly comprising oxides of main group IV and subgroup IV, in particular zirconium dioxide, and in the presence of alcohols.

DE-A-2 519 817 discloses hydrogenating carboxylic acids in the liquid phase, e.g. in the presence of catalysts comprising rhenium and/or elements of subgroup VIII, to give alcohols. This generally requires high temperatures of 200° C. and more and high pressures of 200 bar and more. In many cases, the catalysts cannot be regenerated after their deactivation. If the catalysts contain large amounts of expensive metals, they have to be worked up to recover the metals. If a workup is impossible for technical reasons or economically inappropriate, the spent catalysts have to be landfilled, which is usually very costly.

DE-A-2 543 673 discloses hydrogenating carboxylic esters in the liquid phase or in the gas phase, especially in the presence of catalysts comprising predominantly copper, such as copper chromite catalysts or catalysts comprising copper, manganese and aluminum, to give alcohols. Ester hydrogenations in the liquid phase generally require, like carboxylic acid hydrogenations, temperatures above 200° C. and pressures above 200 bar (WO 97/31882). Ester hydrogenations in the gas phase may be carried out at hydrogenating temperatures around 200° C., but in this case the reaction pressures drop to around 50 bar (U.S. Pat. No. 5,395,990).

Copper catalysts have the disadvantages of being sensitive to halogen contaminants in the starting materials and of a limited catalyst life. Regeneration is impossible in most cases, so that here too a subsequent workup or landfilling of the spent catalysts is necessary.

It is an object of the present invention to develop a process for preparing alcohols by hydrogenation of carboxylic acids and their esters at very low pressure using hydrogenation catalysts which can be regenerated.

First attempts to achieve this are described in the patent literature:

For instance, according to EPA 285 786, carboxylic acids and their esters can be hydrogenated using, as hydrogen transfer agent, alcohols instead of hydrogen, in particular alcohols having 2–6 carbon atoms, to give the corresponding alcohols. Particular preference is given to isopropanol. The reaction is carried out at 250–450° C. and atmospheric pressure in the gas or liquid phase in the presence of only partially dehydrated oxides of zirconium, of titanium or of tin which are prepared, for example, by heating the corresponding hydroxides to temperatures of up to 300° C.

EPA 585 053 discloses reacting carboxylic acids and derivatives thereof, such as esters, nitriles or amides, with alcohols as hydrogen transfer agent in the gas or liquid phase in the presence of $TiO_2/ZrO_2$ catalysts to give the corresponding alcohols. Comparative Example 1 describes, inter alia, the conversion of n-decanoic acid into n-decanol in the presence of only partially dehydrated zirconium hydroxide using isopropanol. At 300° C. and atmospheric pressure, the n-decanol yield is reported as 34% (100% conversion).

According to JP 060 651 25 and JP 060 634 01, it is also possible to use bismuth oxide/$ZrO_2$ and tin oxide/$ZrO_2$ catalysts instead of $TiO_2/ZrO_2$ catalysts.

The use of alcohols as sole hydrogen donor has the disadvantage that the alcohols used for the hydrogenation are converted into the corresponding ketones and hence lost. Since 2 mol of alcohol are used per mole of carboxylic acid or ester and the above-cited literature does not mention the particularly economical methanol as a preferred hydrogenating alcohol, this method is only useful for the preparation of highly priced alcohols.

Finally, JP 6 2108-832-A describes the gas phase hydrogenation of aliphatic and cycloaliphatic carboxylic acids using hydrogen at 200–500° C. and atmospheric pressure in the presence of zirconium dioxide calcined at 300–950° C. and doped with further elements, such as especially chromium to give the corresponding aldehydes and/or alcohols.

In all representation examples of JP 6 2108-832, the hydrogenation is carried out using hydrogen at atmospheric pressure. Cycloaliphatic carboxylic acids such as cyclohexanecarboxylic acid are predominantly converted into cyclohexanecarbaldehyde with 98–99% selectivity using undoped zirconium dioxide at 300–350° C. and atmospheric pressure (Examples 1–7). The aliphatic carboxylic acid pivalic acid yields pivalaldehyde with 100% selectivity (Example 8). However, aliphatic carboxylic acids or their esters having two alpha hydrogen atoms are converted into the corresponding alcohols or mixtures of alcohols and aldehydes in moderate yields and selectivities using chromium-doped zirconium dioxide at 320° C. and atmospheric pressure. For instance, n-heptanoic acid and methyl n-heptanoate produce n-heptanol in a yield of 62% or 33.9%, respectively (Examples 9 and 10), propionic acid (Example 14) and valeric acid (Example 16) produce n-propanol in a yield of 34.6% and only traces of n-pentanol (37.1% n-valeraldehyde yield). Buteric acid (Example 15) produces a mixture of n-butyraldehyde (15.8% yield) and n-butanol (30% yield).

JP 6 2108-832 A does not teach how to convert aliphatic and cycloaliphatic carboxylic acids and esters thereof into the corresponding alcohols in high yields and selectivities. It is merely reported that more alcohol is obtained when the number of carbon atoms in the carboxylic acid is small and that the amount of alcohol increases when the reaction is carried out under pressure.

It is a particular object of the present invention to provide a process which does not have the disadvantages of the abovementioned prior art and which makes it possible to prepare alcohols in very good yields at moderate pressures.

We have found that this object is achieved according to the invention by a process for preparing alcohols by gas phase hydrogenation of carboxylic acids or esters at elevated temperature and elevated pressure in the presence of a catalyst consisting of or comprising, as hydrogenating components, oxides of main group IV and/or subgroup IV, which comprises hydrogenating a) at from 250° C. to 400° C. and from 5 bar to 100 bar in the presence of b) primary or secondary alcohols, preferably methanol, the molar hydrogen/alcohol ratio being at most 800, preferably from 10 to 300 and in particular from 20 to 200.

It was surprising that the specific combination of measures makes it possible to hydrogenate carboxylic acids and esters thereof to give the corresponding alcohols in high yields and selectivities without requiring the high pressures of JP 59106-431 and without dehydrogenating the added alcohols in amounts which would jeopardize economic viability.

Starting materials which may be used in the process of the invention are saturated aliphatic, cycloaliphatic, aromatic and heterocyclic mono- and polycarboxylic acids and esters thereof. Examples are acetic acid, n-hexanoic acid, methyl n-hexanoate, n-decanoic acid, dimethyl valerate, cyclohexanecarboxylic acid, methyl cyclohexanecarboxylate, dimethyl 1,4-cyclohexanedicarboxylate, n-butyl cyclohexanecarboxylate, terephthalic acid, dimethyl terephthalate, methyl benzoate, benzoic acid, nicotinic acid, methyl nicotinate, tetrahydropyran-4-carboxylic acid, methyl tetrahydropyran-4-carboxylate, methyl tetrahydrofuran-3-carboxylate or methyl furan-3-carboxylate or methyl acrylate.

When esters are used as starting compounds, those containing $C_1$–$C_4$-alcohol components are preferred and those containing $C_1$–and $C_2$-alcohol components are particularly preferred.

Useful alcohols are primary and secondary aliphatic, cycloaliphatic, aromatic or heterocyclic alcohols. They should be easily volatilizable under the reaction conditions stated. Preference is given to aliphatic, primary and/or secondary alcohols having 1 to 7 carbon atoms. Examples are methanol, ethanol, n-propanol, isopropanol, n-butanol, sec-butanol, n-pentanol, cyclohexanol, benzyl alcohol. Particular preference is given to methanol, which is not a preferred alcohol in the absence of hydrogen according to EP 585 053 and JP 6 2108-832.

Useful catalysts are oxides of main group IV and subgroup IV, particularly titanium dioxides, zirconium dioxides, hafnium dioxides and tin oxides.

Preference is given to zirconium dioxides which may exist in the monoclinic, cubic or tetragonal crystal lattice form. In particular, zirconium dioxide comprising 50–100%, preferably 60–98%, particularly preferably 70–95% of monoclinic zirconium dioxide is used. These catalysts are commercially available or are obtainable in a conventional manner (see e.g. Catal. Rev. Sci. Eng. 27, (1985), 341–372). They are obtained, for example, by dissolving zirconium compounds, e.g. zirconium nitrate or zirconyl chloride, in water, precipitating zirconium hydroxides using alkali metal hydroxides, alkaline earth metal hydroxides or ammonia, washing of the resulting zirconium hydroxide hydrate, drying and calcining at 300–850° C.

The BET surface area of the zirconium dioxide used is typically from 5 to 150, preferably from 20 to 130, in particular from 40 to 120, m²/g, the term BET surface area as used herein meaning the catalyst surface area as determined by the method of Brunauer, Emmett and Teller (see Z. Anal. Chem. 238 (1968), 187). The zirconium dioxide should be neutral, i.e. contain very few basic and acidic sites. For instance, basic catalyst sites may lead to yield losses, e.g. by aldol condensation of aldehyde intermediates. Acidic catalyst sites may reduce the yields of the desired alcohols by dehydration to give olefins or by formation of ethers.

The $ZrO_2$ catalysts may be used as supported catalysts on a known inert support such as silicon dioxide or aluminum oxide, and especially as unsupported catalysts. They can be used in the form of extrudates, preferably with a maximum diameter of 1–5 mm, pellets or spheres. (All amounts relating to the composition of the catalysts are based on their active mass, i.e. the support materials are not taken into account).

It may be advantageous to add small amounts of one or more elements to the zirconium dioxide to increase the structural stability and the life of the catalyst. Such elements are present predominantly in oxidic form in the finished zirconium dioxide catalyst and are, for example, lanthanide elements such as lanthanum, cerium, praseodymium, neodymium, promethium, samarium, europium, gadolinium, terbium, dysprosium, holmium, erbium, thulium, ytterbium and lutetium.

Compounds of lanthanum and praseodymium and also of cerium, samarium, neodymium and europium are particularly suitable for use as components of the catalysts used according to the invention.

Other elements which may be included are chromium, manganese, zinc, indium, tin, lead, vanadium or iron. Chromium is in particular indicated for the hydrogenation of aliphatic carboxylic acids and esters to give alcohols.

The atomic ratio of the added element to zirconium dioxide is generally in the range from 0.005 to 0.3, preferably in the range from 0.05 to 0.2.

The catalysts may be arranged in a fixed bed reactor or in a fluidized bed reactor. The hydrogenation may be carried out as a downflow or upflow process. It is advantageous to use at least such an amount of hydrogen as hydrogenating agent and carrier gas that starting materials, intermediates and products never become liquid during the reaction. Excessive hydrogen and nondehydrated alcohol are preferably recycled, it being possible for a small part to be bled off as effluent gas in order to remove inert materials such as methane and carbon monoxide. It is possible to use one reactor or more than one reactor, arranged in series or parallel to each other.

The hydrogenation temperature is in the range from 250° C. to 400° C., preferably from 270° C. to 370° C., particularly preferably from 300 to 350° C.

The reaction pressure is in the range from 5 bar to 100 bar, preferably from 10 bar to 60 bar, particularly preferably from 25 bar to 50 bar, when undoped zirconium dioxide is used. The pressure is in the range from 20 to 100 bar, preferably from 30 to 50 bar, when doped zirconium dioxide is used, since the hydrogenation to give the alcohol is apparently retarded by the dopant.

The molar ratio of hydrogen to carboxylic acid or ester used is generally in the range from 20 to 300, preferably from 50 to 150, particularly preferably from 70 to 130.

Deactivated zirconium dioxide catalysts may be regenerated many times e.g. by burning off in air at from 300° C. to 700° C.

The amount of alcohol is generally in the range from 0.5 to 10 mol, preferably from 1 to 5 mol, particularly preferably from 2 to 4 mol, of alcohol per mole of acid or ester used.

The space velocity is usually in the range from 0.01 to 0.3, preferably from 0.05 to 0.2, particularly preferably from 0.05 to 0.15, kg of ester or acid to be hydrogenated per liter of catalyst per hour.

The hydrogenation is preferably carried out continuously. The hydrogenation effluents are condensed and then preferably worked up by distillation.

The hydrogenation effluent consists essentially of the alcohol formed by hydrogenation, alcohol or water released by hydrogenation of ester or acid groups, added alcohol and unconverted acid, ester or aldehyde intermediate. By-products which may occur are olefins, hydrocarbons or ethers. New esters may be formed by esterification or transesterification, but those may be hydrogenated to give the desired alcohols.

Excess added alcohol and, if conversion is incomplete, starting and intermediate compounds present in the hydrogenation effluent may be separated off by distillation and recycled into the hydrogenation step.

EXAMPLES a) Hydrogenation Apparatus:

The runs were conducted continuously in the hydrogenation apparatus shown diagrammatically in FIG. 1. The apparatus consists of an evaporator (E), a 1.4 l tubular reactor (30×2000 mm) (R), two condensers $C_1$ and $C_2$ and a pressure separator (S) for isolating the condensable components from the hydrogen stream, a recycle gas compressor (K) for recycling the recycle hydrogen gas (3) and an effluent tank (T) for collecting the reaction effluent (4).

b) Experimental Procedure:

The zirconium dioxide used in Examples 1 to 7, 9, 11 and 12 was obtained from Norton and had the designation XZ 16075. The zirconium dioxide was in the form of 3 mm extrudates and had a BET surface area of about 50 $m^2/g$. More than 90% of the zirconium dioxide was monoclinic.

In Examples 8 and 10, $La_2O_3$ (3% of La)/zirconium dioxide was used.

The $La_2O_3$ (3% of $La_2O_3$)/$ZrO_2$ was prepared by impregnating 3 mm $ZrO_2$ exdrudates made of $ZrO_2$ from Norton (SN 9516321) with $La(NO_3)_3$ solution, drying at 120° C. for 4 hours and calcining at 400° C. for 6 hours.

In Example 14, $Cr_2O_3$ (5% of Cr)/zirconium dioxide was used.

The $Cr_2O_3$ (5% of Cr)/$ZrO_2$ was prepared by impregnating 3 mm $ZrO_2$ extrudates made of $ZrO_2$ from Norton (SN 9516321) with $Cr(NO_3)_3$ solution, drying at 120° C. for 4 hours and calcining at 400° C. for 6 hours.

The catalyst zone was bounded by a layer of quartz rings at the upper and lower ends. In all cases, recycle gas was used, with 10% of the recycle gas (5) being bled off and replaced by an equal amount of fresh hydrogen.

A pump (P) was used to meter the starting compounds (1), (7), (12) and added alcohol into the evaporator where they were evaporated and passed into the reactor in gaseous form, mixed with preheated hydrogen (2). The molar starting compound/hydrogen ratio of inlet streams 1 and 2 was determined by weighing the amount of starting material added and measuring the hydrogen streams.

The hydrogenation effluent was condensed and then weighed. Its composition was quantitatively determined by gas chromatography using an internal standard (diethylene glycol dimethyl ether). The runs were each conducted for several days without any changes, and only then was the hydrogenation effluent analyzed.

TABLE 1

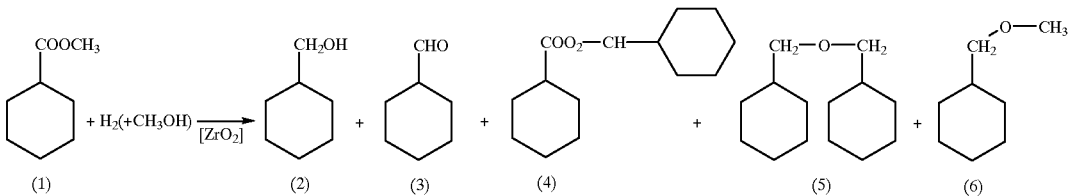

| Example | Temperature [°C.] | Pressure [bar] | Molar ratio ester/$H_2$($N_2$) | Space velocity [kg/l·h] | Methanol addition [mol per mol (1)] | Conversion [%] | Selectivity [%] | | | | |
|---|---|---|---|---|---|---|---|---|---|---|---|
| | | | | | | | Cyclohexane methanol (2) | Cyclohexane aldehyde (3) | Ester (4) | Ether (5) | Ether (6) |
| 1 (Comparative) | 350 | 1 | $H_2$(25) | 0.1 | 0 | 81.9 | 34.6 | 43.7 | 14.5 | 0.7 | 0.2 |
| 2 (Comparative) | | | | | 3 | 73.9 | 68.2 | 14.7 | 8.7 | 0.2 | 1.0 |
| 3 (Comparative) | 330 | 10 | $N_2$(50) | | 3 | 21.0 | 48.7 | 6.0 | 31.9 | 0.9 | 0.8 |
| 4 | | | $H_2$(120) | | 3 | 98.9 | 90.9 | 2.0 | 0.4 | 0 | 3.6 |
| 5 (Comparative) | 330 | 20 | $N_2$(50) | | 3 | 23.8 | 46.5 | 3.8 | 32.2 | 0.9 | 0.8 |
| 6 | | | $H_2$(120) | | 3 | 99.2 | 95.0 | 1.3 | 0.3 | 0 | 5.0 |
| 7 | 330 | 20 | $H_2$(120) | 0.1 | 3[1] | 99.4 | 43.3 | 1.3 | 0 | 17.6 | |
| 8[2] | 305 | 20 | $H_2$(120) | 0.1 | 3 | 99.7 | 96.0 | 1.9 | 0 | 0.4 | |

[1] Three moles of isopropanol instead of methanol
[2] $La_2O_3$/$ZrO_2$ instead of $ZrO_2$

TABLE 2

Benzyl alcohol by hydrogenation of methyl benzoate

| | | | | Space | Methanol | | Selectivity [%] | | | |
| Example | Temperature [° C.] | Pressure [bar] | Molar ratio ester/H₂(N₂) | velocity [kg/l · h] | addition [mol per mol (1)] | Conversion [%] | Benzyl alcohol (8) | Benz-aldehyde (9) | Ester (10) | Ether (11) |
|---|---|---|---|---|---|---|---|---|---|---|
| 9 | 330 | 20 | H₂(120) | 0.1 | 3 | 99.2 | 80.7 | 4.4 | 0.4 | 7.5 |
| 10[1)] | 300 | 20 | H₂(120) | 0.1 | 3 | 100 | 85.0 | 5.2 | 0 | 2.2 |

[1)] La₂O₃/ZrO₂ instead of ZrO₂

TABLE 3

Cyclohexanemethanol by hydrogenation of cyclohexancarboxylic acid

| | | | | Space | Methanol addition | | Selectivity [%] | | | | |
| Example | Temperature [° C.] | Pressure [bar] | Molar ratio acid/H₂(N₂) | velocity [kg/l · h] | [mol per mol (1)] | Conversion [%] | Cyclohexane methanol (2) | Cyclohexane aldehyde (3) | Ester (4) | Ether (5) | (6) |
|---|---|---|---|---|---|---|---|---|---|---|---|
| 11 | 330 | 20 | H₂(120) | 0.1 | 3 | 97.7 | 92.0 | 0.9 | 0.3 | 0.3 | |
| 12 | 330 | 45 | H₂(120) | 0.1 | 3 | 100 | 90.8 | 5.6 | 0.2 | 0.8 | |

EXAMPLE 13

Methyl tetrahydropyran-4-carboxylate was hydrogenated as described in Example 6, but at 310° C./45 bar. The selectivity to 4-hydroxymethyltetrahydropyran was 76.4% (97.4% conversion), the selectivity to 4-formyltetrahydropyran was 2%.

EXAMPLE 14

Methyl n-hexanoate was hydrogenated as described in Example 6, but at 300° C./45 bar and over a Cr₂O₃/ZrO₂ catalyst. The n-hexanol yield was 70% (100% conversion), the selectivity to n-hexanal was 0.5%.

We claim:

1. In a process of preparing alcohols by gas phase hydrogenation of carboxylic acids or esters thereof at elevated temperature and elevated pressure in the presence of a catalyst comprising, as hydrogenating components, oxides of main group IV and/or subgroup IV, the improvement comprising hydrogenating said carboxylic acids or esters
   a) at from 250° C. to 400° C. and from 5 bar to 100 bar in the presence of
   b) primary and secondary alcohols which have been added to the reaction mixture, the molar hydrogen/added alcohol ratio being at most 800.

2. A process as claimed in claim 1, wherein the molar hydrogen/added alcohol ratio is from 10 to 300.

3. A process as claimed in claim 1, wherein added aliphatic primary and/or secondary alcohols having 1 to 7 carbon atoms are used.

4. A process as claimed in claim 1, wherein the alcohol added is methanol.

5. A process as claimed in claim 1, wherein from 0.5 to 10 mol of alcohol are added per mole of starting acid or ester.

6. A process as claimed in claim 1 wherein the hydrogenation temperature is in the range from 300° C. to 350° C.

7. A process as claimed in claim 1, wherein the hydrogenation pressure is in the range from 25 to 50 bar.

8. A process as claimed in claim 1, wherein monoclinic, cubic and/or tetragonal zirconium dioxide is used.

9. A process as claimed in claim 8, wherein the zirconium dioxide used comprises from 50 to 100% of monoclinic zirconium dioxide.

10. A process as claimed in claim 1, wherein the oxide catalyst comprises one or more lanthanide elements or one or more elements selected from the group consisting of chromium, manganese, zinc, indium, tin, lead, vanadium and iron.

* * * * *